US008229872B2

(12) United States Patent
Gilhuly

(10) Patent No.: US 8,229,872 B2
(45) Date of Patent: Jul. 24, 2012

(54) MODELING AND CONTROL FOR HIGHLY VARIABLE AND NONLINEAR SYSTEMS

(76) Inventor: Terence Gilhuly, Vancouver (CA)

( * ) Notice: Subject to any disclaimer, the term of this patent is extended or adjusted under 35 U.S.C. 154(b) by 715 days.

(21) Appl. No.: 12/311,104

(22) PCT Filed: Sep. 14, 2007

(86) PCT No.: PCT/CA2007/001605
§ 371 (c)(1),
(2), (4) Date: Mar. 19, 2009

(87) PCT Pub. No.: WO2008/031208
PCT Pub. Date: Mar. 20, 2008

(65) Prior Publication Data
US 2009/0327204 A1    Dec. 31, 2009

(51) Int. Cl.
*G06F 17/00* (2006.01)
*G06N 5/02* (2006.01)
(52) U.S. Cl. ............... 706/45; 706/52; 706/62; 702/19; 435/3
(58) Field of Classification Search .................. None
See application file for complete search history.

(56) References Cited

U.S. PATENT DOCUMENTS

| | | | | |
|---|---|---|---|---|
| 5,962,317 | A * | 10/1999 | Hamzeh et al. | 435/325 |
| 2003/0203418 | A1* | 10/2003 | Bellinger-Kawahara et al. | 435/8 |
| 2005/0037418 | A1* | 2/2005 | Hamalainen et al. | 435/6 |
| 2006/0089592 | A1* | 4/2006 | Kadhiresan et al. | 604/65 |
| 2006/0167722 | A1* | 7/2006 | MRF Struys et al. | 705/3 |

OTHER PUBLICATIONS

Gilhuly et al. "Modelling for computer controlled neuromuscular blockade", Proceedings of the 2005 IEEE Engineering in Medicine and Biology, 2005, pp. 26-29.*

* cited by examiner

*Primary Examiner* — Omar Fernandez Rivas

(57) ABSTRACT

The present invention relates generally to methods of modeling and handling of nonlinearities for application of automatic control to systems with high inter-process variance and nonlinearities. The variance and nonlinearities make these systems difficult to control. Variance is accounted for by replacing the mathematical model of the system with a more representative model from a modelset that may or may not be chosen based on characteristics of the system under test, and then adapting using recursive estimation techniques. Nonlinearities defined by threshold to response and maximal responses are incorporated into linear models relating accumulated inputs to response. Example implementations in relation to automated drug delivery for neuromuscular blocking drugs through warning, advisory and closed-loop control systems are discussed.

51 Claims, 6 Drawing Sheets

Prior art: modified from reference [19]

average response for population/ subgroup separate modelsets based on demographic/ health parameter most representative model from subset further adaptation by RLSE

MODELING AND CONTROL FOR HIGHLY VARIABLE AND NONLINEAR SYSTEMS

CROSS-REFERENCE TO RELATED APPLICATIONS

The present application claims priority from PCT applications PCT/CA2007/001605 and PCT/CA2008/001606.

BACKGROUND

Many processes have nonlinearities and/or extreme variation between batches (or tests or experiments or subjects or otherwise), and this makes the automation of these processes very difficult. In biological systems, inter-subject (human, non-human animal, tissue or other) variation is large. Parameters describing response to inputs (electrical, chemical or otherwise) vary greatly within the same species, with variation of as much as 50% being common.

The current description, while applicable to any process control system displaying nonlinear behavior and variation, was developed through work done in automated drug delivery in general and automated delivery of neuromuscular blocking (NMB) drugs in specific. Thus, the examples and instantiations presented will concentrate on automated drug delivery. The following discussion provides a general description of certain aspects of the background and while instructive does not provide specific factual representations.

Automated drug delivery (or drug administration under computer guidance or control) can improve drug therapy by allowing for more efficient and smoother delivery. Automated drug delivery may reduce drug usage, side effects and costs; permit health care staff to work more efficiently; and allow the safe use of drugs that are difficult to administer manually, leading to better care for the patient. Computer controlled administration of insulin, blood pressure medications, neuromuscular blocking (NMB) agents and other drugs has been attempted previously with limited success. Application of computer control to NMB drugs is a rich field, and a subject that is both fraught with nonlinearities in response and with great inter- and intra-patient variability. Computer control of NMB drugs will be discussed here to illuminate the difficulties in controlling these nonlinear and variance-prone systems.

NMB drugs produce paralysis to prevent motion, permit tracheal intubation and allow access to deep structures with smaller incisions. As NMB drugs have high therapeutic indices in hospital settings, they are often used in excess of minimal effective requirements. A strategy for administration is to provide an overdose to prolong paralysis, monitor for returning muscle function and, once it returns, overdose again [1]. The large dose delivers rapid onset of paralysis, quicker surgical conditions, and avoids titration to a precise anesthetic setpoint and regulation once there [2].

The practice of serial bolus administration of NMB drugs leads to instances of under- and overdosing. Overdosing is important at the end of the case when the patient should be extubated and awakened, but cannot be due to the presence of too much NMB drug. Overdosing creates delays while the NMB drug wears out and due to improper neuromuscular monitoring, results in a great many patients being extubated prematurely. Incidence of post-operative residual curarization (PORC) is between five and 10% of patients for intermediate-acting compounds, such as rocuronium (Eriksson [3]), and between sixteen and 42% of patients will have To4 measurements of less than 0.7 to 0.8 (Murphy [4]), which can lead to impaired hypoxic ventilatory response and other complications. The overdosing strategy is also a source of inconvenience should complications arise and the surgical conditions change, which is not uncommon. After paralysis and induction have taken place, examination of the patient may reveal a complication such as extensive invasive carcinoma, which may require different staff, equipment and procedures. Changes in staff, equipment and procedures will lead to cancellation of the scheduled procedure, and the anesthesiologist and attending nurses will have to wait until the NMB wears off enough to allow reversal.

As another example, in Harrington rod insertion for reshaping the spine, the surgeon assesses whether or not the rods have impinged nerves by the ability of the patient to respond physically. Testing can be performed only after the return of muscle function. Automatic control could keep the patient less paralyzed until a test is required, reduce drug administration to allow function to return, and then re-paralyze for continued work with less waiting time by the surgical staff.

It is important to avoid underdosing during the case at it can be a source of intra-operative adverse events. Patients with ineffective levels of NMB will cough and buck on the ventilator, possibly resulting in extrusion of internal organs, and will move, possibly resulting in injury from other means. As well, muscles will be tighter and will resist surgical interventions making the surgeons' job more difficult.

The problems associated with serial bolus dosing are intensified due to the current practice in monitoring of NMB being deficient. In an ideal scenario, the patient would be monitored continuously throughout the procedure so that the anesthesiologist and medical staff would be constantly aware of the state of the patient's muscle function and would be able to provide appropriate amounts of NMB drugs to maintain the patient at an ideal level of muscle function throughout the procedure. However, continuous NMB monitoring by the anesthesiologist is labor intensive for someone who—for the betterment of the patient's health—typically cannot devote themselves solely to the NMT sensor. This is one reason why objective monitoring is not done continuously, but instead either only at key points in the case such as extubation, or not at all. Computer control of NMB could reduce anesthesiologists' monitoring of muscle response, reduce loss of reversibility at procedure's end due to over-paralysis, and give anesthesiologists fine control of muscle tone. Representative control efforts include bang-bang [5], Proportional Integral Derivative (PID) control [6], PID/Smith predictor [7] and fuzzy logic control [8]. Some of the controllers developed have not been stable or robust enough to handle the intra- and inter-patient variability present.

Other controllers have achieved near constant levels of blockade in relatively controlled experimental settings, but are associated with significant constraints that thus far have impeded their utility in routine clinical practice. For example, most involve the use of single twitch stimulation to measure response (ST or T1%). In addition to the often considerable associated setup time, the use of single twitch stimulation necessitates a stable control [9] and T1% baseline stabilization requires up to 20 minutes between induction and NMB drug administration [10], unnecessarily exposing patients to the risks of an unprotected airway and creating unacceptable operating room time delays. Furthermore, the typical controller setpoint is T1%=10% (i.e., 90% single twitch suppression) [8, 10, 11, 12] which represents a potentially non-reversible state.

Adaptive control may help accommodate the patient variance. An adaptive controller usually comprises a fixed-structure controller with adjustable parameters and a mechanism for automatically adjusting those parameters. Adaptive control's roots begin in the 1950s with the development of the autopilot for high-performance aircraft [13]. Since then there has been much theoretical development and application. An in-depth review of this field appears in [13]. An example of an adaptive control technique that has been used not just in chemical batch processes but in clinical application as well is Generalized Predictive Control [14, 15], a general-purpose adaptive control method. This method was used in the operating room in control of NMB as described in [16].

Patent Documents

See U.S. Pat. Nos. 2,690,178, 4,080,966, 4,280,494, 4,291, 705 4,370,983, 4,392,849, 4,533,346, 4,741,732, 5,256,156, 5,335,164, 5,409,456, 5,520,637, 5,713,856, 5,822,715, 5,957,860, 6,042,579, 6,186,977, 6,328,708, 6,379,301, 6,389,312, 6,511,453, 6,599,281, 6,605,072, 6,725,086, 6,796,956, 6,807,965, 6,830,047 and 7,220,240; WIPO 93/14807 and 00/67820; and US applications 2006/0217628, 2003/0156143 and 2007/0255135.

BRIEF SUMMARY

Presented here are methods, systems, etc. for reducing variation and the effect of nonlinearities to facilitate application of adaptive control to processes with nonlinearities and/or variation.

Nonlinearities can be accounted for by creating a non-delayable, non-saturatable response model that fully represents the non-linear model through its range of linear response and then adds extrapolation into the ranges in which the non-linear model cannot produce response or in which the nonlinear model produces saturated response, and in this way all inputs can be mapped to an output. To create these models, responses to standard impulses are recorded for one or more processes. Saturated and unaffected (zero or baseline measurements) response measurements are discarded. The remaining points are adjusted by scaling them to be a proportion of the range of effect, and then adding to them an offset to account for the threshold that needs to be achieved before effect is seen. Uninterrupted curves describing these responses can be arrived at through a curve fitting estimation (either linear or non-linear depending upon the linearity of the underlying equations driving the process) of the non-saturated response points correlated to the time since the bolus dose was administered. The uninterrupted curves are linear models of the process impulse responses and can be used as finite impulse responses or converted to transfer function or state space models or otherwise remodeled as desired.

Inter-process variation can be accounted for by substitution for the model in two ways. The first way can be a gross adaptation in which the parameters defining the original model are replaced with the parameters of another model found to be more representative of the process being modeled, according to one or more measured responses judged against the input or inputs given to the process. The substitute model parameters can be taken from a multitude of sets of model parameters (herein referred to as the "modelset") that can be pre-compiled from previous experiments, patient cases or other measurements or other information or calculations as desired. The second way of accounting for variation can be a fine adaptation where linear techniques such as recursive least squares estimation (RLSE) are applied to further tune the model's parameters toward the true parameters.

In one embodiment the methods, etc., discussed herein are incorporated into control of a process having high variability and nonlinear action. The process run is started with the computer or otherwise believing the process to be an average process, and inputs are given to the process based on that information to try to move the system state to a state such that the desired outputs are had. After some inputs are given, the initial delay to action is passed and response is seen. Eventually enough measurements are obtained that the calculation method for determining a suitable model can be made and the parameters describing the model are replaced with a more appropriate set. With every new timestep, input, output and system state data are generated and RLSE is applied to tune the model closer to the true model as a form of continuous improvement. With this continuous improvement the inputs given become more appropriate, the outputs become closer to what is desired and overall performance is improved.

In another embodiment the methods, etc., discussed herein are incorporated into an advisory system in which the input is not given directly by the computer, but is instead given by the user. As in the previous embodiment, the response is sensed, the model is updated, and inputs are calculated through use of the model. However instead of giving the inputs, the calculation results can be presented to the user as advice and the user can decide whether or not to give the input. For a drug advisory system, advice can be provided on how much drug to give and when to give it. The user is generally a health professional, such as an anesthetist in an operating room, but can also be the patient if the drug and advisory system are used in an ambulatory setting.

In another embodiment, the accounting for nonlinearities is used as a method of determining drug concentrations without use of blood sampling.

In another embodiment, the methods, etc., predict likelihood of problems in the process based upon the response measured. For example, based upon a slow response relative to average processes, recommendations might be made to investigate the cause and/or provide preventative maintenance. As another example, a disease state such as liver or renal function diminishment may be predicted in a patient based upon an abnormally long drug residence time. Recommendations can then be made for the patient to undergo testing.

DETAILED DESCRIPTION

Figure 1:
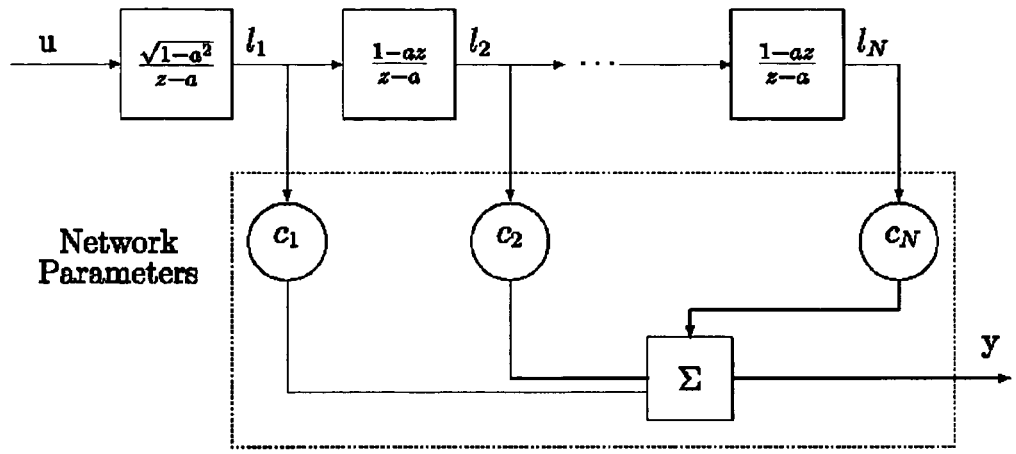
FIG. 1 illustrates a discrete time linear Laguerre model (modified from [19]), where N is the number of filters, a is the Laguerre pole, z is the discrete time forward operator, $I_i$ is the Laguerre vector coefficients and $c_i$ represents the Laguerre gains.

The following discussion begins with a discussion of nonlinearities and how they are managed and incorporated into an exemplary suitable model. A development of the modelsets used for gross adaptation is discussed, and then, a process of model adaptation. Finally, certain embodiments will be discussed.

Process Monitoring

When controlling of a process it is beneficial to know how that process is reacting to input in order to correctly adjust the input, or inputs, to produce the desired output. To learn how the process is reacting, sensors are used. For automated drug administration, there are a great many sensors to measure response to drugs. Heart function is assessed by electrocardiogram (ECG); blood pressure is determined with pressure transducers; and oxygen saturation is determined through use of pulse oxymetry, to name a few. For measurement of neuromuscular response, the sensor stimulates a nerve to evoke contraction of the muscle innervated by that nerve and the contraction can then be measured. Other sensors can be used for non-surgical and non-medical situations, such as optical sensors, digital sensors such as CCDs, CMOSs, CIDs, etc., as well as spectrographic, magnetic, pressure, temperature and other sensors.

For neuromuscular response measurement, the most commonly used neuromuscular sensing modality is the train-of-four measurement (TOF) by electrostimulation. The TOF uses four brief (between 100 and 300 µs) current pulses (maximum of 70 mA) at 2 Hz, repeated every 10 to 20 s as electrostimulation. The resulting twitches are measured and quantified for electromyographic response, force, acceleration, deflection or another means. The first and last pulses produced are compared and the ratio of the two gives an estimate of the level of neuromuscular blockade. Other common stimulation techniques include the single twitch (ST) and post-tetanic count (PTC). The ST measurement is a single electrical pulse of between 100 and 300 µs, repeated at intervals greater than or equal to one second. At least four seconds is desired between stimuli to prevent upregulation and alteration of the true muscle response. An ST measurement taken when the stimulation regime is first started is recorded as the control, labeled T0. The ST measurement is a ratio of the latest measured muscle twitch compared to the T0 value. PTC stimulation is used in deep blockade as a means of evoking a large neurostimulator output in order to overwhelm temporarily the NMB. It consists of a tetanus at 50 Hz for five seconds followed by a three second resting period and then a chain of up thirty ST impulses. The number of impulses that can be measured indicates the degree of blockade.

Modeling

In order to estimate levels of drug in the patient and corresponding response, both at the present and in the future, the controller needs a mathematical description of the process and how the process reacts to inputs. This description is the process model.

Processes can often be described with differential equations. These equations can then be formed into state space models for which a large body of literature has been developed for solving and directing towards control applications, known to those aware of the art. In brief, a general format of a state space model is:

$$x(t+1)=Ax(t)+Bu(t)$$

$$y(t)=Cx(t)+Du(t) \quad (1)$$

where u is the input, y is the output, t is the timestep and x is the state vector, and A, B, C and D are the state, input, output and input-output direct coupling matrices.

An advantageous form of model for administration of drugs and one similar to the state space model is the Laguerre model. A Laguerre model is an orthonormal series representation of a plant's dynamics, consisting of a series of filters, the first being a low-pass filter and subsequent filters being all-pass filters, taking as input the input to the system and producing an estimate of the output. This is displayed in FIG. 1. In the figure, u is the input to the system, y is the output, N is the number of filters, a the Laguerre pole, z the discrete time forward operator, $l_i$ the Laguerre vector coefficients which make up the x state vector of Equation 1 and $c_i$ the Laguerre gains which make up the C output matrix of Equation 1. The matrices A and B are dimensioned by the number of filters and defined by the Laguerre filter pole a. The Laguerre filter pole is optimized for each patient model by a linear search algorithm to provide a best fit of the impulse response data. The C vector parameters are also individual to each patient. Laguerre models are used for their convenient network realization, transient signal similarity (important for responsive process control), and similarity to Pade approximation useful for identifying time delays. Laguerre models have a simple representation and flexible structure, allowing for easy adaptation [17].

Models of response to pharmaceuticals can be composed of two parts. The first part is a description of the drug flow through the subject and is generally a linear differential equation (and thereby easily converted into Equation 1) of the form:

$$c(t) = \sum_{i=1}^{N} a_i e^{-\lambda_i t} \quad (2)$$

where c(t) is the concentration of the drug, $a_i$ is a gain and $\lambda_i$ is the disposition constant for the $i^{th}$ compartment, and N is the order of the compartmental model used to model the drug. For example, the NMB rocuronium is commonly modeled by a third order compartmental model. The second part incorporates the nonlinearities with an equation to convert the concentration of drug present to an effect related to the drug present. Nonlinearities are introduced through such things as delay to activity and saturation of the sensor and/or output from the process input actuator; an example of the former is a water tap being opened only after a certain amount of force is applied to it; and an example of the latter is the inability to increase the flow once the tap has been fully opened.

In some embodiments, nonlinearities are accounted for and the equations representing the system are linearized to allow for application of linear adaptation algorithms. Linear equations have the benefits of easy computation, direct solvability and guaranteed solution. Well-established techniques for control and adaptation of linear models exist and are proven.

Similar to the water tap example, when drugs are administered, measurements can experience nonlinearities in the form of delay to action and saturation of response. These nonlinearities are related to the pharmacological terms of potency and efficacy. Delay can exist because it may be necessary to agonize (antagonize for blocking drugs) a proportion of receptors before response is seen. This apparently non-operational proportion is sometimes known as the "receptor reserve" or "safety factor". Saturation can occur because the maximum response has been met by agonizing all the receptors or a large enough percentage of the receptors to achieve maximum response. Mathematically, these nonlinearities can be seen at low and high concentrations when effect as a function of drug concentration is defined by the sigmoidally shaped Hill equation:

$$E(c) = E_{max} \frac{c^\gamma}{c^\gamma + EC_{50}^\gamma} \qquad (3)$$

where E is effect, E max is the maximum effect possible, c is the concentration of the agent at the effect site, $\gamma$ is the Hill coefficient corresponding to the slope of the curve, and $EC_{50}$ is the effective concentration producing a response 50% of the maximum.

Figure 2:
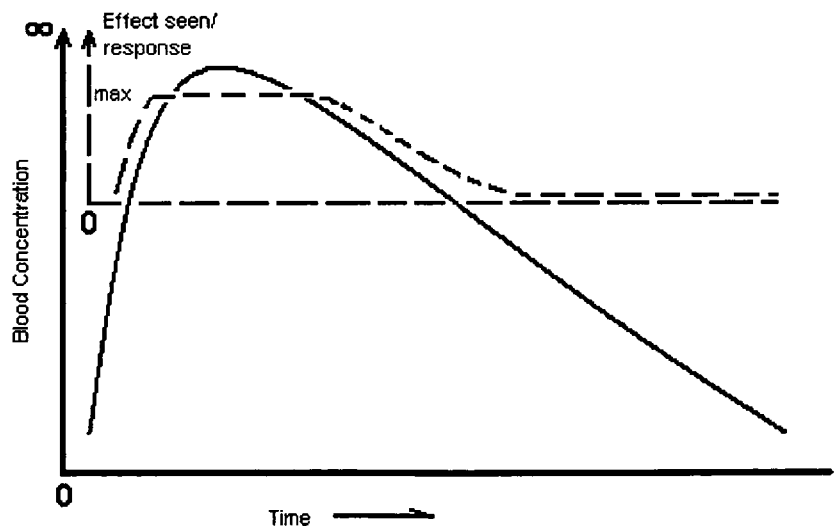
FIG. 2 illustrates a relationship between blood concentration of a drug and response over time. Graphs are overlapped to show that response is not observable until a certain threshold has been reached.

These nonlinearities can be seen in FIG. 2. As drug is added to the patient, the drug is distributed throughout the patient and the concentration at the region of interest begins to rise. At first effect is zero. Then after the drug has enjoined enough receptors, a threshold is reached and effect starts to be seen. Effect increases with concentration to the point of saturation of the response (and/or sensor) after which the measurable effect plateaus. Concentration can continue to rise but there is no increase in effect. Considering only the primary action of the drug and neglecting side effects, concentrations above this level produce no greater effect but instead just extend the amount of time in saturation. Measurable function returns with elimination of the excess drug. Zero effect is seen again once enough drug has been eliminated that the threshold level of drug receptors become free. In the case of NMB drugs, the response measured is contraction which will have a zero effect level of 100% strength. As the drug is an antagonist, the response can be thought of in opposite terms. As drug is added, relaxation (the opposite of contraction) increases.

The neuromuscular junction (NMJ) is an example of a system with receptor reserve. The NMJ, where NMB drugs act, has reserve receptors to increase probability of contraction on stimulation and decrease likelihood of blockade. It also has a saturation level in that an infinite amount of force cannot be generated, and with regards to administration of NMB drugs, after a certain percentage of the receptors are blocked no contraction can be had. In [18], isolated cat anterior tibialis and sartorius muscles were stimulated in the presence of tubocurarine and other NMB drugs at known concentrations. It was estimated that 76±5% of the receptors had to be blocked by the antagonist before block was noticeable, and 92±16% of the receptors had to be blocked for near complete blockade.

In situations in which a computer or other like calculation device is used to aid in calculating and administering the drug or other inputs, the specific details of these models, such as the exact values of the parameters and coefficients found in Equations 1, 2 and 3, will most likely be unknown when the procedure is first started. Instead a best guess at what the values are is used. This guess is usually the parameters learned from prior testing, and can be a population average. Should the best guess differ enough from the values of the true parameters, there will be difficulty in controlling the process with error and/or instability as a result.

References

[1] D. A. Linkens, A. J. Asbury, S. J. Rimmer, and M. Menad. Identification and control of muscle-relaxant anaesthesia. IEE Proceedings-D, 129(4): 136-141, 1982.

[2] R. Miller. "Pharmacokinetics of Muscle Relaxants and their Antagonists", chapter 11 of Pharmacokinetics of Anaesthesia. Blackwell Scientific Publications, 1984.

[3] L. I. Eriksson. Residual neuromuscular blockade: Incidence and relevance. Anaesthesist, 49(Suppl1):S18-19, 2000.

[4] G. S. Murphy, J. W. Szokol, J. H. Marymont, M. Franklin, M. J. Avram, and J. S. Vender. Residual Paralysis at the Time of Tracheal Extubation. Anesthesia and Analgesia, 100: 1840-5, 2005.

[5] C. M. Wait, V. A. Goat, and C. E. Blogg. Feedback control of neuromuscular blockade: A simple system for infusion of atracurium. Anaesthesia, 42:1212-1217, 1987.

[6] B. H. Brown, J. Asbury, D. A. Linkens, R. Perks, and M. Anthony. Closed-loop control of muscle relaxation during surgery. Clinical Physics and Physiological Measurement, 1:203-210, 210, 1980.

[7] D. A. Linkens, M. Menad, and A. J. Asbury. Smith predictor and self-tuning control of muscle-relaxant drug administration. IEE Proceedings-D, 132(5):212-218, 1985.

[8] D. G. Mason, J. J. Ross, N. D. Edwards, D. A. Linkens, and C. S. Reilly. Self-Learning Fuzzy Control with Temporal Knowledge for Atracurium-Induced Neuromuscular Block during Surgery. Computers and Biomedical Research, 32:187-197, 1999.

[9] H. H. Ali, J. E. Utting, and T. C. Gray. Quantitative assessment of residual antidepolarizing block (part I). British Journal of Anaesthesia, 43:473-477, 1971.

[10] P. M. Schumacher, K. S. Stadler, R. Wirz, D. Leibundgut, C. A. Pfister, and A. M. Zbinden. Model-based control of neuromuscular block using mivacurium: design and clinical verification. European Journal of Anaesthesiology, 23:691-699, 2006.

[11] N. R. Webster and A. T. Cohen. Closed-loop administration of atracurium. Anaesthesia, 42:1085-1091, 1987.

[12] T. Mendonca et al. PID control Strategies for the automatic control of neuromuscular blockade. Control Engineering Practice, 6:1225-1231, 1998.

[13] K. J. Astrom. Adaptive Feedback Control. Proceedings of the IEEE, 75(2):185-217, 1987.

[14] D. W. Clarke, C. Mohtadi, and P. S. Tuffs. Generalized Predictive Control—Part I. The Basic Algorithm. Automatica, 23:137-148, 1987.

[15] D. W. Clarke, C. Mohtadi, and P. S. Tuffs. Generalized Predictive Control—Part II. Extensions and Interpretations. Automatica, 23:149-160, 1987.

[16] M. Mahfouf, D. A. Linkens, A. J. Asbury, W. M. Gray, and J. E. Peacock. Generalized predictive control (GPC) in the operating theatre. IEE Proceedings-D, 139(4):404-420, 1992.

[17] C. C. Zervos. Adaptive Control Based on Orthonormal Series Representation. PhD thesis, University of British Columbia, 1988.

[18] W. D. M. Paton and D. R. Waud. The margin of safety of neuromuscular transmission. Journal of Physiology, 191: 59-90, 1967.

[19] G. A. Dumont, Y. Fu, and G. Lu. "Nonlinear Adaptive Generalized Predictive Control and Applications", from Advances in Model-Based Predictive Control. Oxford University Press, Oxford, UK, 1994.

[20] D. M. J. Quastel and P. Pennefather. Receptor Blockade and Synaptic function. Journal of Neural Transmission, Supplemental 18:61-81, 1983.

[21] P. Pennefather and D. M. G. Quastel. Relation between synaptic receptor blockade and response to quantal transmitter at the mouse neuromuscular junction. Journal of General Physiology, 78:314-344, 1981.

[22] M. E. Salgado, G. C. Goodwin, and R. H. Middleton. Exponential Forgetting and Resetting. International Journal of Control, 47(2):477-485, 1988.

Exemplary Handling Response of Nonlinearities

As stated, nonlinearities arise through such things as delay to activity and saturation of the sensor and/or output from the process input actuator. To incorporate the nonlinearities into a linear model so that linear adaptive modeling techniques can be applied, a linear relationship of response and receptor occupancy was developed, called "pseudo-occupancy".

Pseudo-occupancy as applied to non-drug related systems typically does not relate to the occupancy of receptors since many systems do not have "receptors" but does apply to a fundamental aspect(s) of the process relating output to input and will typically be different in name but not in concept.

Pseudo-occupancy is a linearized version of true receptor occupancy and is analogous to the drug concentration at the effector site, e.g. the NMJ in case of NMB drugs. This linearized model of occupancy includes levels greater than 100% (with a range of 0 to infinity) allowing for excessive doses larger than what is necessary to bind all of the receptors, and accounting for the excess drug and how it is metabolized. Pseudo-occupancy can be considered a total of how many multiples of the amount of drug to bind to all of the receptors is present at the effector site. Response data are converted to pseudo-occupancy as:

$$pseudoOccupancy = response \times \frac{pseudoOccupancy\ range}{effect\ range} + threshold \quad (4)$$

$$= response \times \frac{1 - threshold}{max\ response} + threshold$$

where max response is the maximal response measurable by the sensor being used (or a set maximum for the sensor, which can be less than the sensor's ultimate sensitivity) and threshold is the pseudo-occupancy level at which the effect produced by the input can first be seen.

For administration of NMB drugs, the maximal effect occurs when either there are no more free receptors or when the sensor is saturated and no longer registers response. A suitable value for the threshold was found through a nonlinear curve fitting of data from [20, 21] to the Equation 3 for response to ST stimulation at the NMJ according to the proportion of receptors free of drug, resulting in:

$$response(FR) = \frac{FR^{3.7}}{FR^{3.7} + 0.2^{3.7}} \quad (5)$$

where FR is the proportion of free receptors, the Hill slope γ was found to be 3.7, and the 50% response was found with 20% of the receptors being free. Then, the curve of Equation 5 was linearized by retaining its slope and 50% response datapoint of 20% receptors free. Extending this new curve revealed an intersection with 0% effect (no relaxation) at a free receptor ratio of approximately 0.3, indicating that 70% of the receptors would be blocked at the point where the ST response started to decay. To determine a threshold for the more commonly used TOF measurement, a correlation between ST and TOF was constructed based on equivalent measurements between the ST and TOF measurements and a pseudo-occupancy of approximately 50% was found to be the threshold.

Building the Modelset

As there is generally some difference between the initial model of the process and the true model, there can be some error initially and success of the controller will be defined by how quickly the model can be adjusted to match the true model. Rapid adjustment can be achieved by replacement of the original model's parameters with more representative ones from a modelset, where "modelset" refers to a multitude of sets of parameters determined for related and relevant process models. The modelset comprises a group of like-representation processes, similar in mathematical construct but different in parameters of the model.

Figure 3:
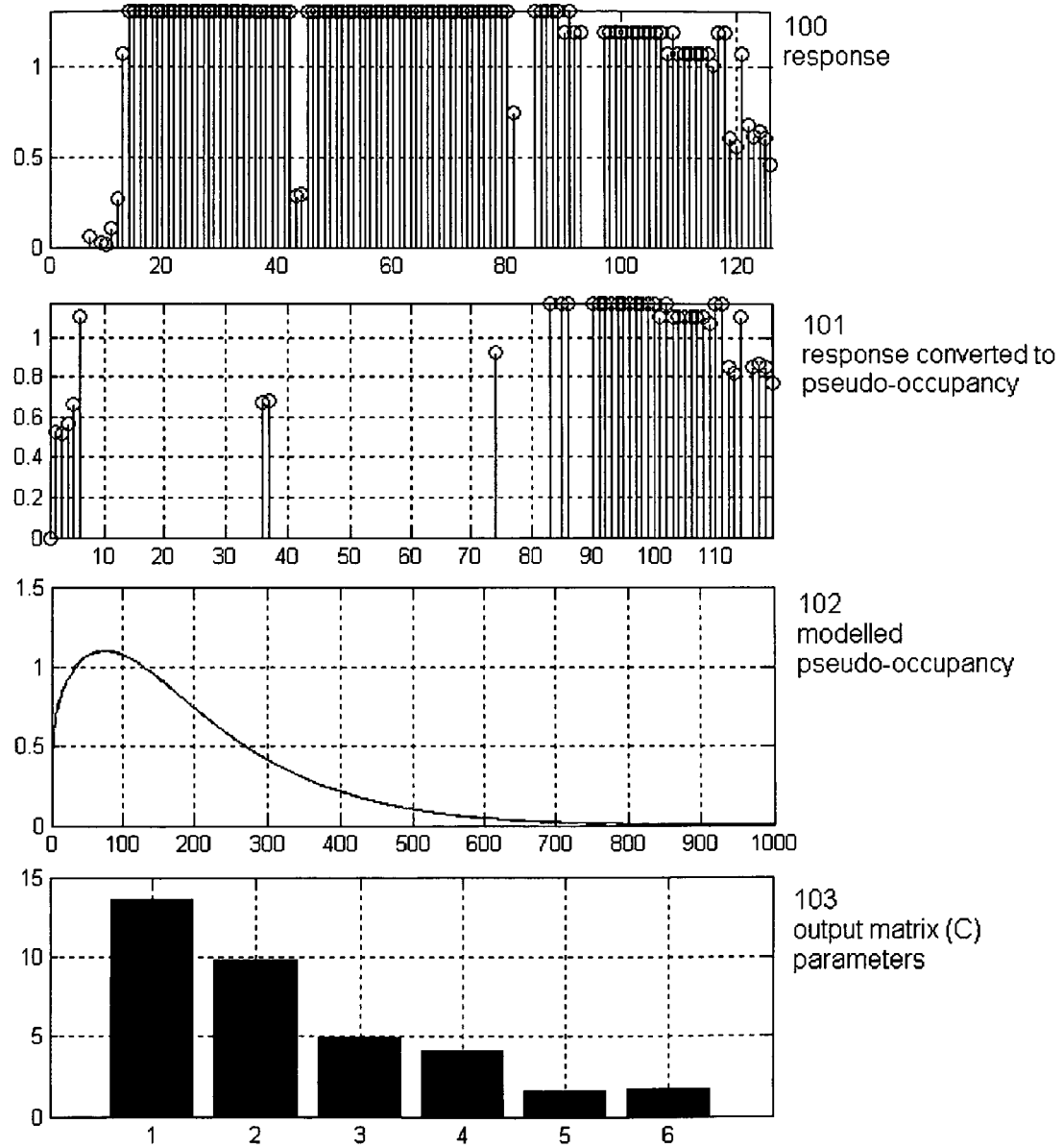
FIG. 3 illustrates the modeling process where response data is converted into pseudo-occupancy data, modeled as an impulse response and then modeled as a state space model.

In one embodiment, the modelset can be built by repeating the steps described below and as graphed in an example in FIG. 3 (minor steps not shown), for a multitude of subject processes. These steps can include:

1. A standard input is given to a multitude of subject processes and the response recorded 100. The input is chosen based on the expected range of response and the qualities of the inputs. For drug administration saturation is desired but not toxicity. An exemplary dose is the 2×ED 95 dose.
2. A dataset of matched output and time datapoints is assembled from the non-zero and non-saturated points, and adjusted for nonlinearities 101. Some zero value response points may be added at future times to force the estimation to return to zero as would happen once the drug is completely eliminated.
3. The dataset may be adjusted for non-unitary inputs. For drug administration, the dataset could be scaled by the ratio of the 2×ED 95 dose to the dose given.
4. An estimation of the parameters of the equations of the model of response is calculated. In one embodiment, the response is in terms of pseudo-occupancy and/or the non-linearities have otherwise been incorporated. The estimation can be done using a recursive nonlinear estimation on a Taylor expansion of the model's defining equations.
5. Full time-courses for the input according to its governing equations can be generated 102. For each model, the model's estimated parameters are inserted into the equation and impulse responses are calculated for a reasonable amount of time, preferably until the modeled response falls below a level considered to be noise.
6. Should the model have parameters that can be optimized, optimal parameters are found. For the Laguerre model, the optimal Laguerre pole for each response can be found using the calculated impulse response data and an iterative search over the full range of possible poles.
7. Should the model be a Laguerre or other similar state space model, modeling of the filter gains for each process' modeled impulse response can be done 103. This can be done using a least squares estimation of the parameters (here, the parameters can make up the output gain matrix, C) of Equation 1, as:

$$\underline{C} = (\underline{x}^T \underline{x})^{-1} \underline{x}^T \underline{y} \quad (6)$$

where $\underline{x}$ is a matrix of the state vectors x, calculated using A and B matrices and compiled as:

$$\underline{x} = [x_0 | x_1 | \ldots x_N] \text{ and } \underline{y} = [y_0, y_1 \ldots y_N]^T \quad (6a)$$

a vector of measured responses.

8. An average model can be created by modeling the average of all the responses.

Conversion to a model format with the optional steps of 6 and 7 in this embodiment is advantageous. The model could remain an impulse response however there is typically greater computation required based on the size of the vectors involved. Responses to impulse dosing of rocuronium were found to be on the order of 1000 timesteps, which would be unwieldy in application of adaptation techniques. In one embodiment the modelset is composed of impulse responses constructed from previous uses of the control system. In the case of drug administration, the previous cases can be gathered in preclinical trials of the controller. Other commonly used model formats for which parameters could be generated and stored for reference include autoregressive models (ARMA, ARMAX and Box-Jenkins models, for example), transfer functions and zero-pole models.

As the controller is used with more processes and the responses to the input(s) are modelled and recorded, the number of processes in subgroups (subpopulations) based on shared characteristics will grow. For example in medical applications, patients can be classified (grouped) according to demographics (age, sex, height, weight, race, . . . ) and health conditions (such as liver, kidney and heart failure), As the number of patients in a subgroup becomes sizeable, a statistically meaningful average response can be calculated or otherwise determined for the processes within that subgroup. This subgroup average model can then be used instead of the overall population average response model as the initial model (the user would facilitate this by entering patient data prior to the procedure to classify the process). This grouping can thus be used to reduce variance between the initial model and the actual process by using a subgroup response model that should bear more resemblance to the true response. The accumulation of responses and the development of the subgroups and subgroup models is a method of continual improvement of the control system and a method of reducing the variation in each of these groups. This process can be seen in FIGS. 6 and 7, where FIG. 6 demonstrates an exemplary generalized procedure and FIG. 7 shows an exemplary process with use of subgroups. In one embodiment, impulse response models are constructed through the use of the control system and the modelset is increased in size by adding more impulse responses to the modelset as the responses are gathered.

In a further embodiment, characteristic data related to the processes is gathered, stored, and used for the purpose of classification and grouping of the process models into related subgroups. In one embodiment the storage is in the form of a database, relational or otherwise, with or without the model parameter values. For automated drug administration, the data gathered can include demographic data such as age, sex, weight, height, lean body mass, body mass index, racial, genetic and otherwise. The data gathered can also include data related to lifestyle such as smoking status. The data gathered can further include information related to health conditions such as kidney function, mean arterial blood pressure, hypertension and diabetes.

In one instance the initial model is an average, mean, mode or otherwise compiled model constructed from the available historical data from prior use of the controller. In another instance, the initial model is an average, mean, mode or otherwise compiled model of a subgroup of the available models selected according to shared characteristics. Should faster performance be desired, the initial model can be chosen to be a model of lower response relative to the models that would otherwise be selected in the previous two instances. This will cause the controller to deliver more input to reach the setpoint and will thereby on average get to it faster. Alternatively should safety be the most important criteria and overshoots in response undesirable, the model can be selected to be one that would have a higher response.

In one embodiment, processes for which the system (controller, advisor or other instantiation) has already been used can use the impulse response calculated at the previous use of the system as the initial model. For example, a patient returning for a follow-up procedure can use the model data from their previous procedure. As intrapatient variability does occur there is a chance that the patient's response may have changed and therefore adaptation from the original model may still be desired. An example of this is the development and/or progression of kidney disease reducing drug clearance and thereby extending effect.

In another embodiment, a central dataset exists and at the end of the control procedures, process model and characteristic data is sent to and compiled within the modelset. This central dataset may be central to the organization in which the system is being used, such as in a hospital, or may be central to political organizations such as cities, countries or otherwise, or may be central to the planet as a whole. Sending of the model and data to these central databases can be via wireless or wired means, over a network including intranets and the Internet.

Model Adaptation

Based upon the response(s) seen to the input given, adaptation of the model parameters is performed to improve the model, make it more closely resemble the specific process, and thereby improve the error performance by calculating and administering more accurate inputs. As the process is not completely known to the computer on their first meeting, the model for the patient response to the drug being advised upon or controlled can only be guessed at. As a best estimate the response is set to the population average response. This likely will not be the correct model but, assuming a normal distribution of responses, it will be close enough. Adaptation of the model can be performed to reduce error due to mismatch. The system of this work improves upon the model in two ways: model swapping and recursive estimation.

Model Swapping

As a rule-of-thumb for some embodiments, adaptation is capable of handling patient model parameter variation of about 30%. Model swapping—substitution of another model's parameters for the current model—can provide gross tuning to reduce the error in the model parameters to levels manageable by adaptation. As frequent model swapping can lead to instability, it is typically only done a limited number of times, and preferably model swapping is only done once. With a substantial enough modelset, one swap can be sufficient to ensure stability and improve error performance to the point of acceptability.

As an example of this, NMB drug is given to a patient undergoing a procedure requiring paralysis. As the operation proceeds, data is gathered for the level of blockade seen (the output), drug given (the input) and the modeled patient occupancy level. After an appropriate number of iterations of patient stimulus, blockade measure and drug level adjustment, the current model is compared to the other models within the patient's subgroup (or in the overall population should the numbers of previously measured patients falling into the subgroup not be great enough). Calculations are made for what response would be had (what level of blockade would be seen) with the drug inputs given, for models having the parameters of the other patient models. A best model is chosen based on least error and the current model (subgroup or population mean) parameters are replaced by those of the best matching pre-recorded individual model based upon the closest matching calculated response. Should the initial model prove to be the most representative, substitution is not required.

In one embodiment model swapping takes place after a pre-determined number of datapoints where that number would be sufficient enough to allow an appropriate decision to be made. This can be through a rule-of-thumb approach of allowing a certain number of datapoints per model present in the modelset, e.g. two measurements required per model in the modelset. In another embodiment, model swapping takes place after an event. For drug administration, this event can be after a certain number of doses or an arrival at a certain level of function or after a pre-defined amount of time has passed.

In another embodiment, swapping takes place if the computer senses that the model is sufficiently incorrect.

In another embodiment, the user forces swapping to take place. This may be because they feel the model is unrepresentative.

In another embodiment there are precautions and error correction in place to ensure that the model is not swapped for a model that is less representative of the current process. Some examples of possible actions are: performing the remodeling as needed—e.g. no model swap if the model parameters are within 20% of the model started with at the time of model swapping; excluding potentially incorrect models from the modelset—e.g. should the process look like it responds at a degree higher than average, do not allow model swapping to a model that responds to a degree lower than average; and rejecting the model selected in the model swapping process if it is a clear mistake—e.g. a process responding as a high responder should not be replaced with a low responding model.

Model Adaptation through Recursive Estimation

Once the initial modeling is completed, RLSE can be used to update the gain parameters (the C matrix) as new information in terms of output and process state are received. RLSE can be performed using the Exponential Forgetting and Resetting Algorithm (EFRA) as developed in [22]. The equations describing this algorithm are the following:

$$e(t+1) = y(t+1) - L^T(t+1)C(t) \quad (7)$$

$$C(t+1) = C(t) + \frac{\alpha P(t)L(t+1)}{\lambda + L^T(t+1)P(t)L(t+1)}e(t)$$

$$P(t+1) = \frac{1}{\lambda}\left(P(t) - \frac{P(t)L(t+1)L^T(t+1)P(t)}{\lambda + L^T(t+1)P(t)L(t+1)}\right) + \beta I - \gamma P(t)^2.$$

where these are equations for error: e(t+1); the new parameter update: C(t+1); and for the error covariance matrix: P(t+1).

The EFRA parameters can be modified as the case progresses to reflect a better understanding of the patient. The forgetting factor, λ, can be increased from its starting value to retain more information believed to be more reliable (i.e. representative of the potentially changing patient). For example, the forgetting factor can be increased from 0.95 to 1.0. As well, the parameters β and γ can be reset to zero, as parameters β and γ are not desired once the forgetting is turned off (at λ=1.0). This update can occur when a certain number of doses have been given or when a certain number of measurements of response have been recorded. Also, the parameters can be modified according to factors known to affect response to the drug being advised upon, such as temperature and the presence of other drugs, to reduce the forgetting in times of greater certainty and increase the forgetting when these factors have a greater influence (in order to maintain fast adaptation), such as when there is sufficient volatile anesthetic to affect the NMB. RLSE is desirable at all times (even before the remodeling point at which models are switched and adaptation potentially lost) to avoid situations of under-actuation where too little input is given to overcome the threshold. This can happen if too little drug is given and then the system is unable to get data for remodeling, as can happen with low responders. The system can then be stuck waiting for the model to correct itself and eventually the user may have to intervene.

For the benefit of other calculations such as determination of remaining drug in the patient and the calculation of infusion rates, an impulse response representation of the patient's drug flow can be maintained as well. If a different model format is used, the impulse response may need to be updated as well. Due to the likely large size of the vectors used, solution of Equations 6 and 8 will be impractical. Thus, the other format can be used in a manner similar to giving an impulse to a state space model and evaluating repeatedly until the response has decayed below a level considered the threshold for noise.

Figure 6:
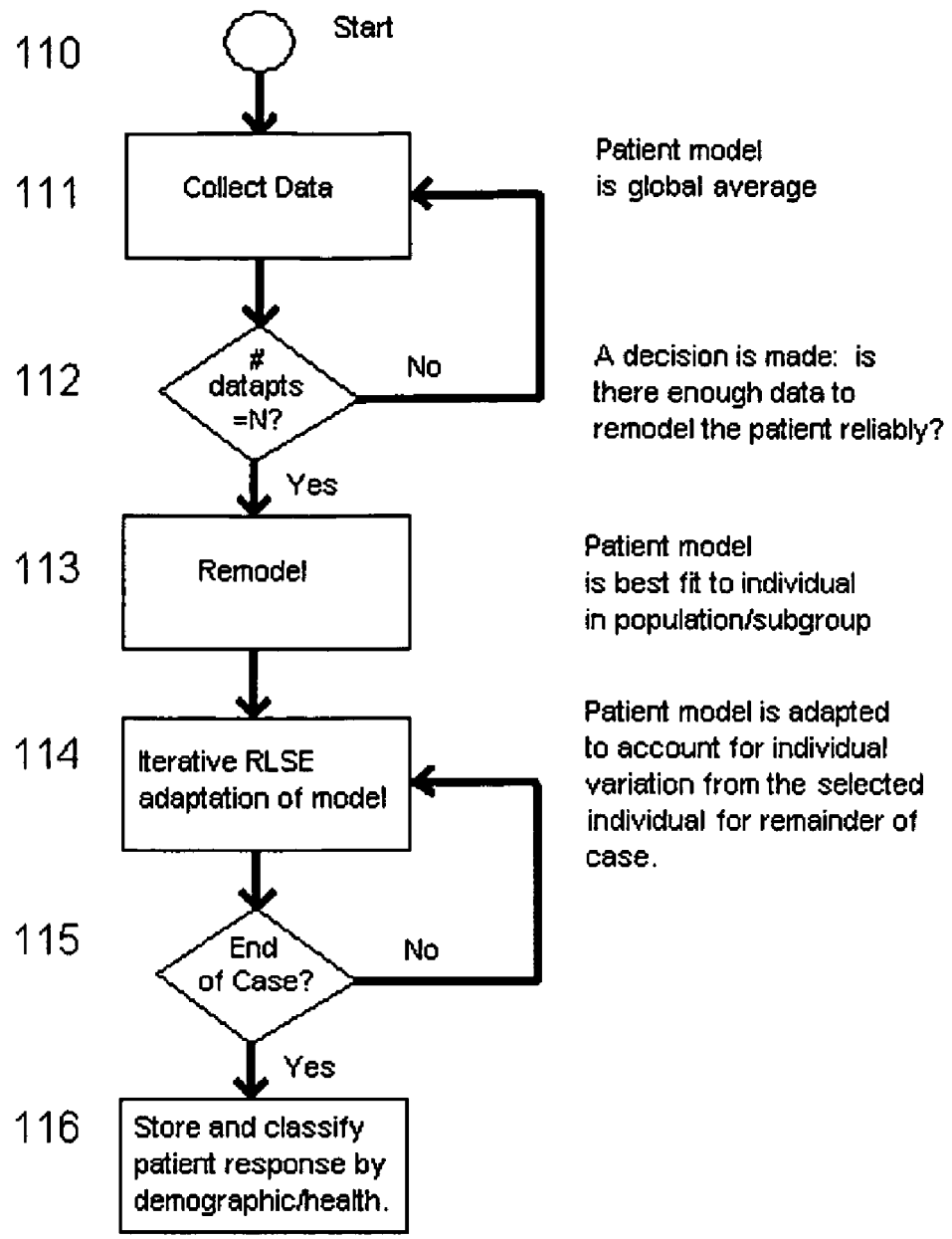
FIG. 6 illustrates a modeling procedure of model replacement and adaptation.
Figure 7:
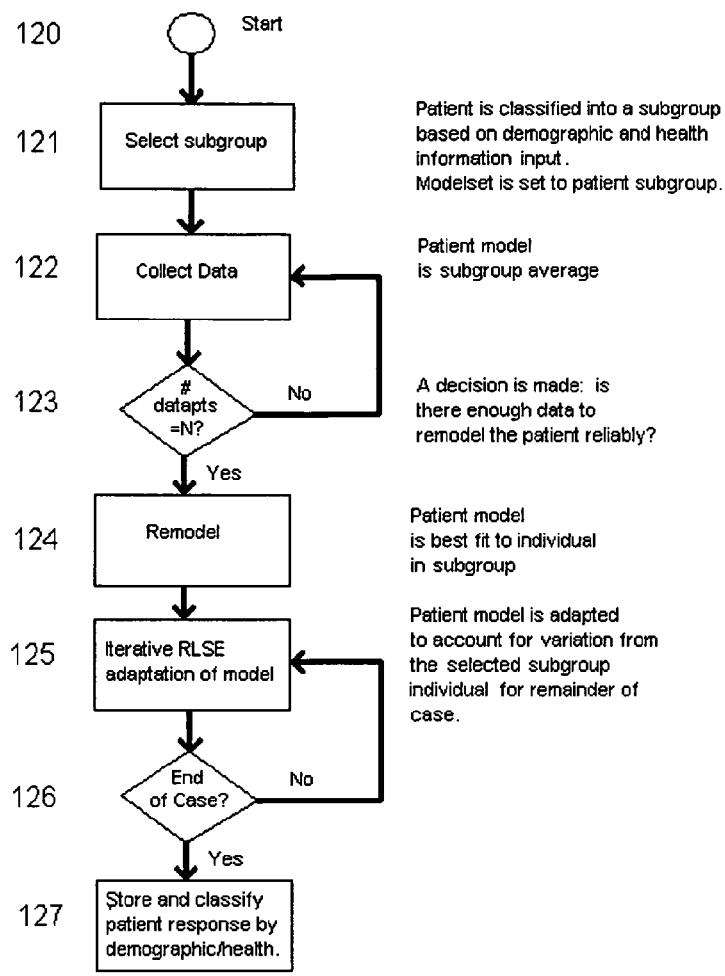
FIG. 7 illustrates a modeling procedure of model replacement and adaptation with subgroups.
Figure 8:
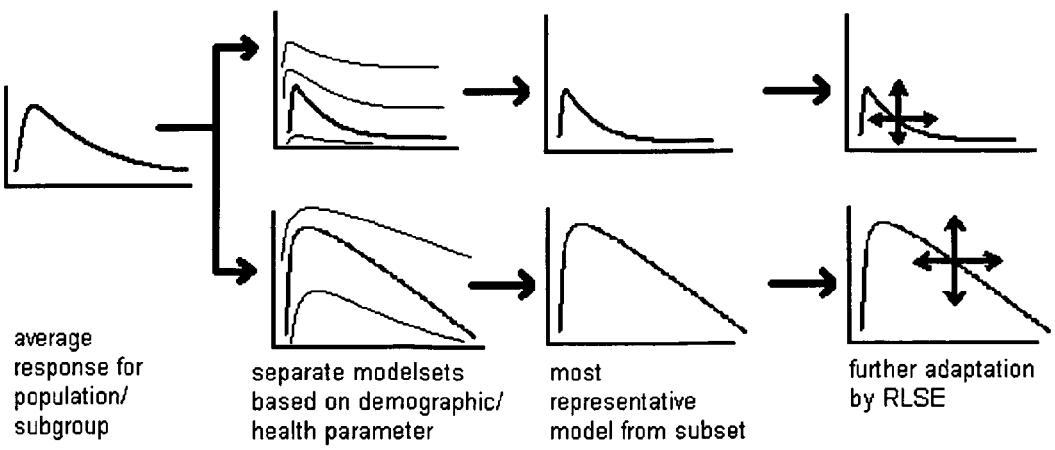
FIG. 8 illustrates a modeling procedure viewed schematically.

As desirable instantiations, flowcharts of the model adaptation procedure are shown in FIG. 6 for a full dataset and in FIG. 7 for a model adaptation procedure in which subgroups are used. At the start 110 of the procedure the process model begins as the global average. Data collection 111 of response, model state and inputs given starts and continues as long as the system is in use. After each timestep, conditions are checked to see if it is time for a model swap. Step 112 compares the number of datapoints accumulated against a predetermined desired amount and once it is reached the model swap takes place at step 113. After the model swap, RLSE adaptation of the model 114 is performed until the end of the case 115 is reached. Once the end of the case 115 has been reached, storing of the model and process characteristics is performed 116. Storage can be in a database, relational or otherwise.

For the procedure in which subgroups are used, the procedure can start 120 with the model undetermined. In step 121 the user enters data relating to characteristics of the current process. This data is then used to identify a subgroup of processes similar to the current process based upon the indicated process characteristic data. A model can be compiled from this subgroup's models that may or may not be an average of this modelset subgroup. The case then proceeds as it did for the previous described instantiation with data collection 122 of response, model state and inputs given; a decision on having enough data points to make a model swap 123 followed by model swapping at step 124 if enough have been collected; RLSE adaptation of the model 125 until the end of the case 126; and storing of the model and process characteristics 127.

Exemplary Instantiations

Implementation of Advisory Systems. In one instantiation, the methods of accounting for nonlinearities and adapting for variance are incorporated into an advisory system for giving inputs indirectly through an intermediary user. An example of this is an advisory system for drug administration, which can make dosing recommendations—how much and when—to the user based on measured patient response and an internal model of the patient. The user is generally a health professional such as an anesthesiologist but also potentially the patient if the methods, etc., are incorporated into an ambulatory device. The initial dose is determined by manufacturer's recommendations or an appropriate dose for the patient's population subgroup.

Subsequent doses are adjusted to adapt to the individual's response to the drug. As use proceeds the advisory system learns the response for each patient and is better able to predict the optimum dose desired. At all times the user can have the final say on what is given, making this a very safe device to use in a clinical setting as all advice will be questioned, and backed or rejected based on medical experience.

Figure 4:
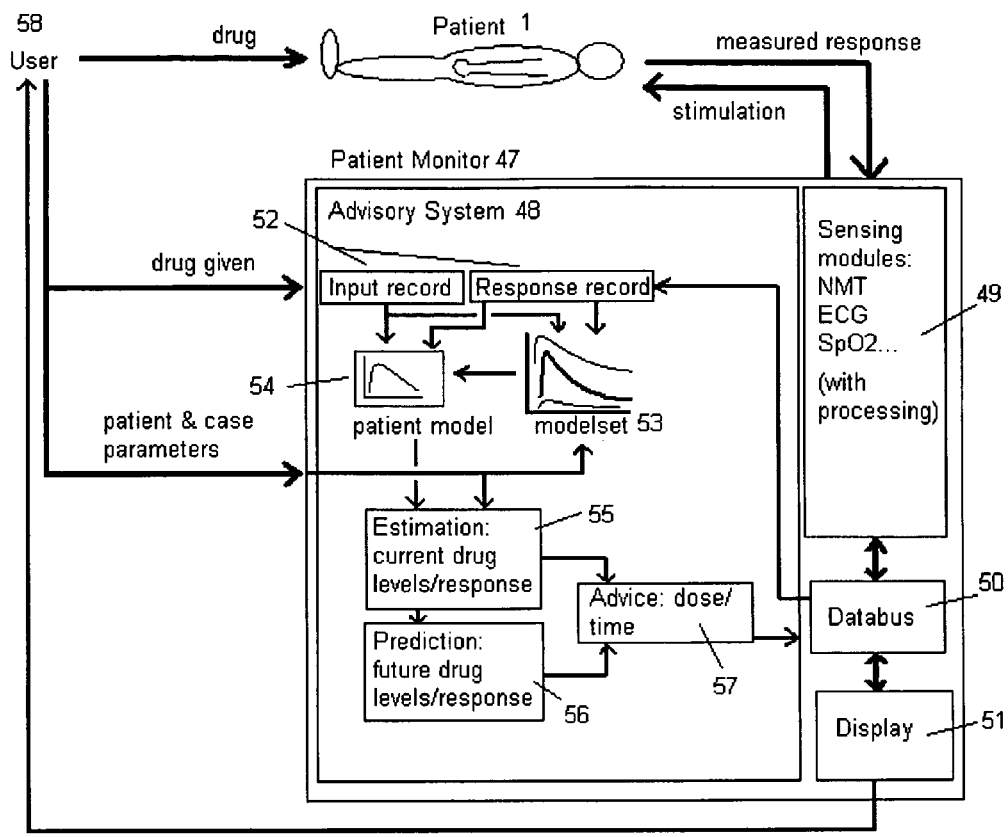
FIG. 4 illustrates a block diagram of an advisory system.

A block diagram of an advisory system for administration of drugs appears in FIG. 4, as it would be incorporated into a module retained inside a patient monitor 47. The patient monitor 47 is further comprised of sensing modules with processing 49, display 51, a databus 50 to interconnect the subcomponents and possibly other advisory system modules. Also in the system are the patient 1 and the health professional user(s) 58. The patient monitor 47 interacts with the patient 1, sending stimuli to elicit response if necessary (passive sensors such as the ECG do not do this) and receiving response data for processing and display to the user 58. The user 58 gives drug to the patient 1, and information on drug administered (should there be no automatic feedback of this data), and patient and case details to the patient monitor 47.

The advisory system 48 receives data on drug given from user 58 and response data from sensing module 49 via databus 50 and stores the data in the input and response records 52. The advisory system also receives data on the patient and case parameters to aid selection of an initial mathematical model of the patient response 54 from the modelset 53 and for use by the other procedures. Other procedures include algorithms for adaptation of the model 54 to better suit the patient, for estimating current drug levels and response 55, prediction of future drug levels, responses and time to those levels and responses 56, and generation of advice 57. Finally advice from advice generator 57 is presented to the patient monitor via databus 50 for display to the user 58.

Figure 5:
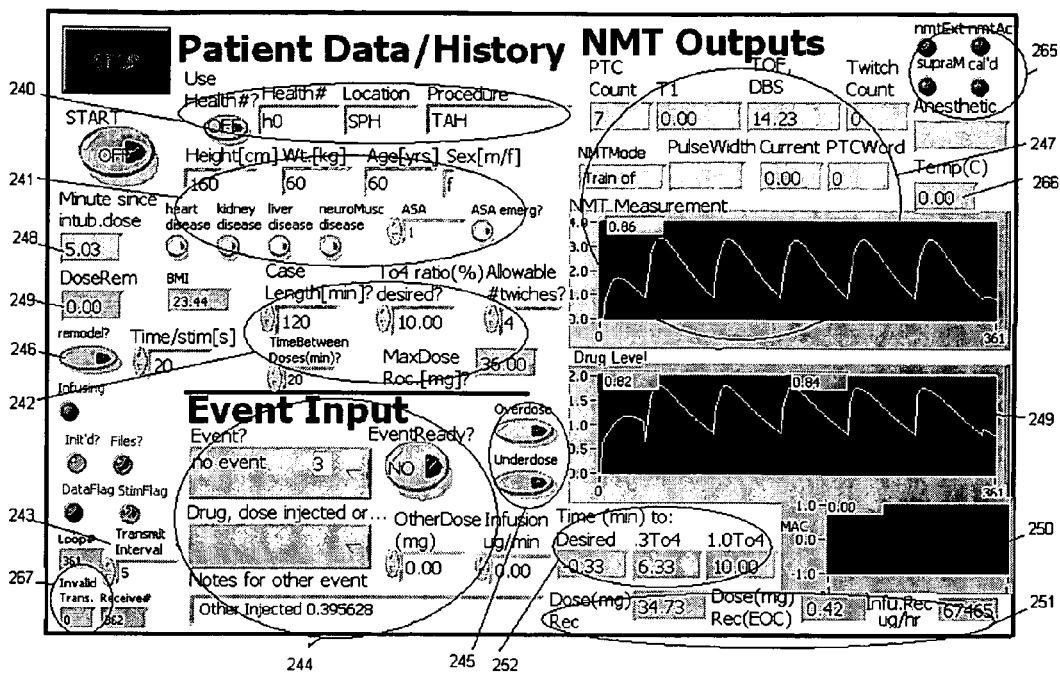
FIG. 5 illustrates a sample depiction of the NMBAS display.

A version of a user interface for the advisory system used for the administration of NMB drugs appears in FIG. 5. Inputs are on the left hand side of the screen with hospital 240, patient 241 and case related data 242 at the top, and event input 244 at the bottom. Outputs are on the right hand side, with NMB measurement data 247 at top (status variables, raw and charted data below that); estimated drug level 249 information charted below that; and predictions 252 until the response returns to the level of the user's indicated setpoint, the level of function returning and until reversal.

The user interface displayed was used in clinical testing of the NMB Advisory System, and is an engineering prototype. It is presented here for explanatory purposes. Future versions of this instantiation of the systems, methods, etc., herein can have a user interface more organized to the workflow of the physician using the device, possibly with data display and inputs organized according to function, for example as patient data, sensor output and hardware setup. The user interface of FIG. 5 was displayed on a laptop computer and, with NMBAS incorporation as software into a patient monitor, would likely be changed for congruity with the user interface of the monitor as a whole. Similarly, if the systems, methods, etc., herein are made as standalone units or otherwise adapted for a given project, including non-drug-monitoring projects, the display would most likely change to reflect workflow and size restrictions.

The advisory system can receive as input prior to the case: unique identifiers of the patient, their procedure and the hospital; patient (e.g., comprising age, sex, height, weight and race) demographics and health conditions (e.g., comprising major organ pathologies and relevant diseases); details of the case aiding operation of the advisor including predicted case-length to provide an endpoint so that predictions of amounts of drug needed to arrive at the desired setpoint at the end of the case can be made; the desired time between doses to set the lesser amount of time between doses or adjustments of the infusion rate to avoid continual adjustment and administration of small amounts; and other pertinent data. In one embodiment with reference to FIG. 5, the advisory system receives as inputs from the user(s) during the case: details of clinically important events 244 such as the amount of drug administered and when it was administered and events important for record keeping; corrections to the model 245 should the computer's model of the patient be apparently flawed (e.g. indication of suspected overdose or underdose conditions); and others.

In one embodiment, throughout the case the advisory system can present outputs to the user including for example: details of measurements 247; minutes since intubating dose 248; estimates 249 of the current and historical levels of drug in the patient and corresponding estimates of response to those approximated levels as numerical and/or graphical data; patient physiological data 266 such as temperature; anesthetic use 250 and other relevant drugs; advice 251 for doses to arrive at the desired response in the desired time between doses and at the predicted end-of-case would be displayed as well as recommended infusion rates; estimated time to desired endpoints 252; sensor status 265; equipment status 267 and transmission interval 243. Also shown is remodel input 246 which can be used to force a remodeling.

In another instantiation of an advisory system, the advisory system can inform the user on the length of time until indicated response levels are reached. For example, with an NMB advisory system it may be desired to know when the response will recover to a desired level (e.g. TOF of 10%), when the patient can breathe spontaneously (judged to be a TOF of 70%), and when the patient can be considered reversed (a TOF of 100%.) Analogous endpoints for other drugs would be the length of time until a desired response is seen, until the drug is no longer effective and until the drug is eliminated from the patient completely.

The time to these events can be determined by advancing the model in time until the level of drug falls enough that the response desired is reached. The number of timesteps desired to do so converted to units of time is the answer. Calculations are performed for the model, modified for no-input conditions:

$$x(t+1)=Ax(t)+Bu=Ax(t)$$

$$y(t)=C^T x(t) \quad (8)$$

This is performed iteratively while increasing time t until the desired level is reached or until the maximum time horizon of concern (this is needed to prevent infinite calculation) is exceeded.

Thus, the systems, methods, etc., herein can serve a warning system and alarm, to warn of impending events and to alert the user if events are possible. An example of the usefulness of this is the clinical application of an advisory system for NMB drugs. Warning of impending return to a level at which the patient can move allows the attending user to prepare and administer more NMB drug, preventing that motion, reducing risk of injury to the patient and allowing the surgery to proceed more smoothly. Similarly if the patient is capable of motion and the advisor either senses this or predicts it with its modeling function, the attending user can be alerted and act accordingly.

An estimate of the amount of input remaining is recalculated each timestep, or a desired number of timesteps, to keep up with impulse response changes due to model adaptation and the diminishing effects of the inputs as time proceeds. An exemplary method is a summing of the convolution of the impulse response with the input history vector over a recent period of time equivalent to the time-length of the impulse response. For example, consider a patient whose impulse response lasts 300 timesteps, and who has received drug at timestep 0 and 200. At timestep 350 this patient will substantially have no remaining drug due to the first dose and will have remaining drug because of the second dose proportional to the area under the curve of the impulse response between relative timestep 150 (from current timestep: 350, subtracting the timestep of administration: 200) and the end of the impulse response.

In one embodiment, the advisory system predicts what the future inputs such as drug inputs, should be to arrive at the desired levels of response. In one instantiation, an extended horizon predictive controller is applied to derive the input repeated each timestep that will arrive at the desired setpoint at a desired time, N number of timesteps, into the future. Starting from the initial state equation, assuming a constant input and extrapolating into the future:

$$x(t+1) = Ax(t) + Bu(t) \quad (9)$$
$$x(t+2) = Ax(t+1) + Bu(t+1)$$
$$= A(Ax(t) + Bu(t)) + Bu(t+1)$$
$$= A^2 x(t) + (ABu(t) + B)u(t)$$
$$\ldots$$
$$x(t+N) = A^N x(t) + (A^{N-1} + A^{N-2} + \ldots + I)Bu \quad (10)$$

where the second equation was arrived at by substituting the first equation for x(t+1). The future response will be $y^R = C^T x(t+N)$ and the current response is $y(t) = C^T x(t) x(t)$. The input desired to get from the present state to the future state can be found by subtracting the two responses and then solving for u:

$$y_R - y(t) = C^T(x(t+N) - x(t)) \quad (11)$$
$$= C^T(A^N x(t) + (A^{N-1} + A^{N-2} + \ldots + I)Bu(t) - x(t))$$
$$u = \frac{y_R - y(t) - C^T(A^N - I)x(t)}{C^T(A^{N-1} + A^{N-2} + \ldots + I)B}$$

For bolus-style, discrete inputs, there are no other inputs between this input, u(t), and the next predicted dose and Equation 11 reduces to:

$$u = \frac{y_R - y(t) - C^T(A^N - I)x(t)}{C^T A^{N-1} B} \quad (12)$$

As another exemplary method of prediction for a system in which discrete inputs are given in an overdose and recovery fashion, the interval between application of inputs is measured and recommendations are for repeated doses if there is sufficient time until the end of the case or fractional inputs are determined and recommended based on the ratio of time remaining to the time between standard doses.

In a second instantiation for calculating infusion rates, the rate is considered as a method of replacement of drug lost over the timestep. Drug removed can be found by calculating the drug remaining in the patient at the current time and subtracting what drug remains in the next timestep.

In a third instantiation, the infusion rate is determined by classic pharmacological methods by using the expected clearance rate, Cl, and the desired concentration in the plasma at steady state, $C_{pSS}$:

$$\text{infusion rate} = Cl \times C_{pSS} \quad (13)$$

This approach may not be very useful outside of the average case, as it typically cannot tolerate variation in patient parameters. The pharmacokinetic terms have to be known exactly and specifically to the patient undergoing the procedure.

In a fourth instantiation, infusion recommendations are made by calculating the repeated doses needed for horizons of increasing size up to the desired endpoint, and then averaging to get the final overall value recommended. The dose at each timestep is calculated according to Equation 11. It is mathematically possible to have negative values depending on the circumstances, such as if the current measurement is at a higher response than the desired future response. Therefore, another version of the average dosing approach is a constrained version in which only the positive values are included in the average.

In the above an extended horizon predictive control scheme was used. Other control methods include for example generalized predictive control, minimum variance and moving average stochastic control, linear quadratic control, self-tuning control and pole placement control.

EXAMPLE IMPLEMENTATION: A Neuromuscular Blockade Advisory System (NMBAS) advises anesthesiologists on rocuronium dose magnitude and timing for maintenance of NMB at surgically favorable, yet easily reversible levels. A prospective randomized, controlled clinical trial was conducted to investigate NMBAS safety and effectiveness, testing the hypotheses that NMBAS is at least as safe as, and provides better care as compared to standard practice.

A prospective, randomized, controlled, clinical trial was conducted with n=73 patients (ASA physical status IIII) undergoing abdominal surgery under general anesthesia=1.5 h with neuromuscular blockade using rocuronium. Patients were allocated to standard care or NMBAS-guided rocuronium administration. The primary outcome variable was the incidence of intraoperative events reflecting inadequate NMB. Secondary outcome variables included train-of-four (TOF) ratios at reversal and extubation; the total doses of rocuronium, reversal agents, anesthetics, and other drugs; the incidence of postoperative adverse events, and the incidence of anesthesiologist non-compliance with NMBAS recommendations.

Of 73 enrolled patients, n=30 per group were eligible for analysis. Patient demographics were comparable between the groups. The incidence in total intraoperative events associated with inadequate NMB was significantly lower in the NMBAS group compared to standard care (8/30 vs. 19/30; p<0.01). Mean TOF ratios prior to reversal were higher in the NMBAS group.

Compared to standard practice, NMBAS guided care was associated with improved NMB quality and higher TOF ratios at extubation, potentially reducing the risk of residual NMB and improving perioperative patient safety.

Closed-Loop Control Systems

In another instantiation of the invention, the techniques taught are integrated into a closed-loop control system. Operation can be similar to the advisory systems described except the inputs are given directly to the patient. This system could be much like other closed-loop controllers with feedback of measured response except the modeling procedure would follow the described approach of model swapping from a modelset, and with continuous update of the parameters through estimation techniques. As well, nonlinearities of the processes that this is applied to can be incorporated into the models of the modelset.

Bloodfree Determination of Drug Concentrations

Blood sampling is normally desired for determining the concentration of drug agent, either NMB drug or otherwise, in the blood and other tissues when performing pharmacokinetic modeling. This can be done when the result is not needed immediately. In an operating room where automated control is to be used, the time desired to get the blood sample, analyze it and report its value, not to mention the manpower and money, is not available. This is especially true with the changing nature of the patient condition and the faster kinetics of some drugs.

In another aspect of the invention, instantaneous drug concentration is approximated without blood sampling by relating response measured to inputs given through a continually updated model. With knowledge of the relationship between the response and receptor occupancy, translation between the two can take place. As well, since the blood concentration can be related to receptor occupancy within the applicable range up until full occupancy, blood concentrations of drugs can be approximated by the measured response. This is advantageous as it eliminates the need for blood sampling.

To emphasize this process in the terms of pharmacokinetic (body effect on the drug) and pharmacodynamic (drug effect on the body) modelling, as blood levels are not available, insight into the organism-drug system is through the sensor output. The patient model is a pharmacokinetic model approximating concentrations of the drug in the patient. This model is adapted to reflect what is seen in the pharmacodynamics, the response measured by the sensors. Thus, an estimate of the blood levels can be had based on the measured response.

Prediction of Process Problems

The response measured and its corresponding model may vary substantially from the other models in the overall group or subgroup as selected by process characteristics. As well, the response and corresponding model may be similar enough to other models of processes seen that had known problems. Thus, in another aspect, the process model that is revealed through adaptation, in use of the controller or advisor or other system incorporating these methods, can be used to predict the status and condition of the process under test.

In one example, a chemical process demonstrating a slow response may be in need of maintenance. Once the control system recognizes this in the response, recommendations can be made to the user that they investigate the cause and provide preventative maintenance. As patient health can dictate the pharmacokinetics of a drug in the patient, the inverse may also be true: measurement of the patient response may reveal information as to the health of the patient and show classification into a particular subpopulation cluster. As an example of this, based on the response model, predictions can be made as to the state of specific conditions of health and organ pathologies (e.g., liver function) related to the aspects of pharmacokinetics (absorption, distribution, metabolism and excretion). In an exemplary use of this, an automated administrator of rocuronium might notice that the patient has an abnormally long elimination of the drug relative to the other members of the patient's subgroup. The automated administrator can then indicate to the user this fact and recommend that the patient undergo testing for kidney and liver function. In another exemplary use of this, the converse may also reveal information on the patient's health: if the patient's response is found to be significantly shorter than the normal response, this might indicate their metabolism has been made faster. The faster response could indicate thyroid issues, metabolic disorders and potentially cancers.

Furthermore should the process's response be identical, or nearly so, to a particular subpopulation response, the process may be a candidate for joining that subgroup and testing can be advised. For example, if a patient without previous heart problems whose response resembles the response of the heart-failure subpopulation (and this subpopulation's responses are substantially different the normal population), then the patient may want to undergo testing for the particular condition.

Terms

All terms used herein, are used in accordance with their ordinary meanings unless the context or definition clearly indicates otherwise. Also unless expressly indicated otherwise, the use of "or" includes "and" and vice-versa. Non-limiting terms are not to be construed as limiting unless expressly stated, or the context clearly indicates, otherwise (for example, "including", "having" and "comprising" typically indicate "including without limitation"). Singular forms, including in the claims, such as "a", "an" and "the" include the plural reference unless expressly stated, or the context clearly indicates, otherwise.

Unless stated specifically, patient refers to any biological system, human or other animal. While examples pertain more to human application, veterinary and experimental and other applications are included.

While the systems, methods, etc., herein have been described with specific reference to administration of NMB drugs, it is understood that the systems and methods taught herein can be applied to other drug therapies and other processes. Furthermore, the systems and methods taught herein can be applied beneficially to modeling and control (advisory and otherwise) of systems with non-negligible parameter variation.

From the foregoing, it will be appreciated that, although specific embodiments have been discussed herein for purposes of illustration, various modifications may be made without deviating from the scope of the discussion herein. Accordingly, the systems and methods, etc., include such modifications as well as all permutations and combinations of the subject matter set forth herein and are not limited except as by the appended claims or other claims having adequate support in the discussion herein.

What is claimed is:

1. A method of adapting a model of a process comprising at least one equation said equation including a set of at least one parameters, said model translating at least one input into at least one response, and said model beginning as at least one of an initial model taken from a modelset comprising one or more models of like processes similar in mathematical construct but with one or more differences in the at least one parameters or built as a mathematical function of models in the modelset comprising:

(a) collecting measurement data related to at least one measured responses;

(b) estimating model parameters to adapt the model of a process to the collected data; and (c) evaluating said model of a process for comparative performance versus other process models in the modelset, and replacing the at least one parameters of the model of a process with the set of at least one parameters of another similar in mathematical construct process model from the modelset.

2. The method of claim 1 where the modelset is comprised of models created by:

(a) administering a standard input given to a process receiving at least one inputs and producing at least one responses, said process having nonlinearities of at least one of a minimum input or minimum amount of accumulated input to produce a non-minimal response and a maximum response;

(b) recording the one or more responses produced by the standard input;

(c) assembling a dataset of matched response and time datapoints where response datapoints comprise non-minimal and non-maximal response measurements, and time datapoints comprise time of measurement;

(d) adjusting the dataset to correct for the nonlinearities on a second scale accounting for said nonlinearities where the process is modeled as linear on the second scale, by converting the response data according to a slope defined as the range of inputs or range of accumulated inputs that produces a range of measurable responses that are neither minimal nor maximal responses, divided by said range of measurable responses over said range of inputs or accumulated inputs; and offset defined as an input or quantity of accumulated inputs required to establish a non-minimal measurable response; and calculating the adjusted response on the second scale as the measured response multiplied by said response plus the offset;

(e) estimating at least one parameters for at least one mathematical function to describe the adjusted dataset; and (f) calculating at least one continuous set of datapoints described by the at least one function whose at least one parameters are estimated in step (e).

3. The method of claim 1 where estimating the at least one parameters includes at least one of least squares estimation, recursive least squares estimation and recursive least squares estimation with forgetting.

4. The method of claim 3 where the at least one parameters are modified according to a recursive least square estimation algorithm with forgetting and the parameters for forgetting are modified.

5. The method of claim 1 where the modelset is associated with a database of one or more sets of characteristic data related to one or more processes whose process response models have been included in the modelset.

6. The method of claim 1 where the probability of deterioration of the process is estimated by comparison of the process response to response models within the modelset known to be deteriorated.

7. The method of claim 6 where the at least one inputs are drugs and the process represents a patient, and where presence of metabolic conditions or organ failures is predicted based on comparison of the adapted response model to response models of patients known not to have said metabolic conditions or organ failures.

8. The method of claim 6 where the process is a patient, the at least one inputs are drugs and the deterioration of the process relates to the presence of a specific disease, and the specific disease is detected by comparing the model to patient models of a subset where the patients are known to have the specific disease.

9. A system for indicating when at least one response of a process will reach at least one setpoint, the system comprising:

(a) a user interface for receiving process related data including process characteristics and inputs administered, and for displaying information including warnings;

(b) a communications interface through which the system obtains data from at least one sensor;

(c) a model of the process' at least one response comprising at least one equation said equation including a set of at least one parameters, said model translating at least one input into at least one response;

(d) a computing mechanism operatively connected to the communications interface to receive the sensor data and connected to the user interface to receive input from the user and to present data to the user, the computing mechanism configured to use the model of the process' at least one response to estimate current and future responses;

(e) memory operatively connected to the computing mechanism for storing and retrieving sensor data and data relevant to the computation, and for storing programs for operation by the computing mechanism; and (f) a modelset comprising one or more models of like processes similar in mathematical construct but with one or more differences in the at least one parameters;

where said model begins as at least one of an initial model taken from the modelset or is built as a mathematical function of the models in the modelset, and is adapted by steps comprising:

(i) collecting measurement data related to at least one measured responses;

(ii) estimating the at least one parameters to adapt the model of a process to the collected data; and (iii) evaluating said model of a process for comparative performance versus other process models in the modelset, and replacing the at least one parameters of the model of a process with the set of at least one parameters of another similar in mathematical construct process model from the modelset.

10. The system of claim 9 further comprising a database of characteristic data related to the processes whose process response models have been included in the modelset.

11. The system of claim 9 where the process is a patient, and the at least one responses includes a physiological response, a concentration of at least one drug or an effect due to at least one drug.

12. The system of claim 11 further comprising a database of characteristic data including demographic data, health and lifestyle related data associated with the processes whose process response models have been included in the modelset.

13. The system of claim 10 where the model of the process is evaluated for comparative performance with models in the modelset sharing characteristics in common with the process as indicated by data in the database of characteristic data.

14. The system of claim 13 where the process represents patients and the model of the process is evaluated for comparative performance with models in the modelset having similar demographic parameters that comprise at least one of age, sex, weight, height, lean body mass, body mass index, race, genetic data and history of smoking.

15. The system of claim 13 where the process represents patients and the model of the process is evaluated for comparative performance with models in the modelset having similar health characteristics that comprise at least one of heart failure, lung failure, liver failure, kidney failure, hypertension and diabetes.

16. The system of claim 15 where the process is evaluated for comparative performance with models in the modelset based on degree of disease or disorder progression.

17. The system of claim 11 where the drug is a neuromuscular blocking agent.

18. The system of claim 9 where the system further advises a user on how much of at least one input to administer to a process, such that at least one response of a process will reach at least one setpoint, (a) where the user interface for receiving process related data including process characteristics and inputs administered, and for displaying information including warnings further displays advice; and (b) where the computing mechanism operatively connected to the communications interface to receive the sensor data and connected to the user interface to receive input from the user and to present data to the user, the computing mechanism configured to use the model of the process' at least one response to estimate current and future responses, further calculates quantities of the at least one input to be administered to arrive at a future desired response level.

19. The system of claim 18 further comprising a database of characteristic data related to the processes whose process response models have been included in the modelset.

20. The system of claim 18 where the process is a patient, the at least one input is a drug, and the at least one responses includes a physiological response, a concentration of drug or an effect due to at least one drug.

21. The system of claim 20 further comprising a database of characteristic data including demographic data, health and lifestyle related data associated with the processes whose process response models have been included in the modelset.

22. The system of claim 19 where the model of the process is evaluated for comparative performance with models in the modelset sharing characteristics in common with the process as indicated by data in the database of characteristic data.

23. The system of claim 22 where the process represents patients and the model of the process is evaluated for comparative performance with models in the modelset having similar demographic parameters that comprise at least one of age, sex, weight, height, lean body mass, body mass index, race, genetic data and history of smoking.

24. The system of claim 22 where the process represents patients and the model of the process is evaluated for comparative performance with models in the modelset having similar health characteristics that comprise at least one of heart failure, lung failure, liver failure, kidney failure, hypertension and diabetes.

25. The system of claim 24 where the process is evaluated for comparative performance with models in the modelset based on degree of disease or disorder progression.

26. The system of claim 18 further comprising adaptation of the model through estimating model parameters by at least one of least squares estimation, recursive least squares estimation and recursive least squares estimation with forgetting.

27. The system of claim 26 where the model is adapted according to a recursive least square estimation algorithm with forgetting and the parameters for forgetting are modified.

28. The system of claim 20 where the drug is a neuromuscular blocking agent.

29. The system of claim 9 where the system further administers in a closed loop fashion at least one input to a process, such that at least one response of a process will reach at least one setpoint,
  (a) where the computing mechanism operatively connected to the communications interface to receive the sensor data and connected to the user interface to receive input from the user, the computing mechanism configured to use the model of the process' at least one response to estimate current and future responses, further calculates quantities of the at least one input to be administered to arrive at a future desired response level;
  (b) and where the system further comprises output communication means to at least one drug input means to automate the at least one drug inputs.

30. The system of claim 29 further comprising a database of characteristic data related to the processes whose process response models have been included in the modelset.

31. The system of claim 29 where the process is a patient, the at least one input is a drug, and the at least one responses includes a physiological response, a concentration of drug or an effect due to at least one drug.

32. The system of claim 31 further comprising a database of characteristic data including demographic data, health and lifestyle related data associated with the processes whose process response models have been included in the modelset.

33. The system of claim 32 where the model of the process is evaluated for comparative performance with models in the modelset sharing characteristics in common with the process as indicated by data in the database of characteristic data.

34. The system of claim 33 where the process represents patients and the model of the process is evaluated for comparative performance with models in the modelset having similar demographic parameters that comprise at least one of age, sex, weight, height, lean body mass, body mass index, race, genetic data and history of smoking.

35. The system of claim 33 where the process represents patients and the model of the process is evaluated for comparative performance with models in the modelset having similar health characteristics that comprise at least one of heart failure, lung failure, liver failure, kidney failure, hypertension and diabetes.

36. The system of claim 35 where the process is evaluated for comparative performance with models in the modelset based on degree of disease or disorder progression.

37. The system of claim 29 further comprising adaptation of the model through estimating model parameters by at least one of least squares estimation, recursive least squares estimation and recursive least squares estimation with forgetting.

38. The system of claim 37 where the model is adapted according to a recursive least square estimation algorithm with forgetting and the parameters for forgetting are modified.

39. The system of claim 31 where the drug is a neuromuscular blocking agent.

40. A method of describing a measured response from a process receiving at least one inputs and producing at least one responses, said process having nonlinearities of at least one of a minimum input or minimum amount of accumulated input to produce a non-minimal response measurement and a maximum response measurement, on a second scale accounting for said nonlinearities where the process is modeled as a process linear on the second scale, by converting the response according to a slope and offset comprising:
  (a) defining said slope as the range of inputs or range of accumulated inputs that produces a range of measurable responses that are neither minimal nor maximal responses, divided by said range of measurable responses over said range of inputs or accumulated inputs;
  (b) defining an offset parameter as an input or quantity of accumulated inputs required to establish a non-minimal measurable response; and
  (c) calculating the second response as the measured response multiplied by said response, plus the offset.

41. The method of claim 40 where the offset is modified from its normal value for the process to replicate at least one abnormal process.

42. The method of claim 40 where the process is a patient, the at least one inputs are drugs, the at least one responses is a physiological response and the second scale describes an estimate of receptor occupancy.

43. The method of claim 42 further comprising converting the estimate of receptor occupancy to an estimate of drug present.

44. The method of claim 42 where the process relates to neuromuscular blockade and the inputs are neuromuscular blockade drugs; the at least one response is a neuromuscular response; and the offset is the percentage of receptors blocked before effect is detectable.

45. The method of claim 44 where the neuromuscular response is evoked by train-of-four (TOF) stimulation, the offset is at least about 50% of receptors blocked and the maximum effect is found when no response is elicited from said TOF stimulation.

46. The model of claim 45 where the offset is reduced to simulate a muscular disorder or disease.

47. A method of calculating a linear response model for a process receiving at least one inputs and producing at least one responses, said process having nonlinearities, where said nonlinearities include at least one of a minimum input or minimum amount of accumulated input to produce a non-minimal response and a maximum response, comprising:
 (a) administering at least one standard input to the process;
 (b) recording one or more responses produced by the standard input;
 (c) assembling a dataset of matched response and time datapoints where response datapoints comprise non-minimal and non-maximal response measurements, and time datapoints comprise time of measurement;
 (d) adjusting the dataset to correct for the nonlinearities on a second scale accounting for said nonlinearities, where the process is modeled as a process linear on the second scale by converting the response data according to a slope defined as the range of inputs or range of accumulated inputs that produces a range of measurable responses that are neither minimal nor maximal responses, divided by said range of measurable responses over said range of inputs or accumulated inputs; and an offset defined as an input or quantity of accumulated inputs required to establish a non-minimal measurable response; and calculating the adjusted response on the second scale as the measured response multiplied by said response plus the offset;
 (e) estimating at least one parameters for at least one mathematical function to describe the adjusted dataset; and
 (f) calculating at least one continuous set of datapoints described by the at least one function whose parameters are derived in step (e).

48. The method of claim 47 further comprising converting the continuous set of datapoints with a state space representation.

49. The method of claim 47 where a Laguerre representation of the model is used and filter gains are calculated from the continuous set of datapoints.

50. The method of claim 47 where the parameters for the at least one mathematical function are derived through nonlinear estimation.

51. The method of claim 47 where the process is a patient and the at least one input is a drug and said input includes at least one of the manufacturer's recommended dose, an effective dose in 95% of the patients (ED95) and double the ED95 dose.

* * * * *